United States Patent [19]

Short et al.

[11] 4,197,186

[45] Apr. 8, 1980

[54] HYDROCARBON CONVERSION

[75] Inventors: Glyn D. Short; Michael S. Spencer; Thomas V. Whittam, all of Stockton-on-Tees, England

[73] Assignee: Imperial Chemical Industries Limited, London, England

[21] Appl. No.: 911,193

[22] Filed: May 30, 1978

[30] Foreign Application Priority Data

Jun. 1, 1977 [GB] United Kingdom ............... 23112/77

[51] Int. Cl.$^2$ ...................... C10G 11/02; C10G 11/04; B01J 29/06
[52] U.S. Cl. ................................. 208/120; 252/455 Z
[58] Field of Search ..................... 252/455 Z; 208/120; 423/328, 330

[56] References Cited

U.S. PATENT DOCUMENTS

| 3,565,788 | 2/1971 | Foucher, Jr. et al. | 252/455 Z |
|---|---|---|---|
| 3,640,905 | 2/1972 | Wilson, Jr. | 252/455 Z |
| 3,686,121 | 8/1972 | Kimberlin, Jr. et al. | 252/455 Z |
| 3,764,520 | 10/1973 | Kimberlin, Jr. et al. | 208/120 |
| 3,769,202 | 10/1973 | Plank et al. | 208/120 X |
| 3,894,940 | 7/1975 | Scherzer et al. | 208/120 |
| 3,925,195 | 12/1975 | Scherzer et al. | 208/120 |

FOREIGN PATENT DOCUMENTS 1088159 10/1967 United Kingdom ................ 252/455 Z

*Primary Examiner*—Carl Dees
*Attorney, Agent, or Firm*—Cushman, Darby & Cushman

[57] ABSTRACT

A catalyst for hydrocarbon conversion contains a silica-containing material having a plate or sheet morphology, for example "FU-1" and a material having catalytic activity for hydrocarbon conversion, for example rare-earth exchanged zeolite Y. The catalyst is especially suitable for cracking heavy fractions to naphtha-type products, apparently because the plate or sheet material provides channels by which large molecules can gain access to active centers in the catalyst.

10 Claims, No Drawings

HYDROCARBON CONVERSION

THIS INVENTION relates to hydrocarbon conversion catalysed by a new, preferably zeolite-containing, composition.

We have found that silica-containing materials having a plate or sheet morphology, especially zeolites and particularly the zeolite-like material FU-1, which is described in our co-pending application U.S. Ser. No. 845,391 filed Oct. 25, 1977 and published on May 9, 1978 as Netherlands Application 7712173, can be used as a component of a hydrocarbon conversion catalyst containing one or more other materials providing an acid function effective in hydrocarbon conversion reactions; and that such a catalyst can afford properties of activity, resistance to deactivation, feedstock acceptance or product distribution, or more than one of these properties, that increase the efficiency with which feedstock oils can be converted to valuable products. In particular, such catalysts are effective in cracking large molecules such as alkyl naphthalenes and hydrogenated naphthalenes. It is believed that the plate or sheet morphology may give rise to channels by way of which such molecules can gain access to active centres in the catalyst.

According to the invention a catalyst for hydrocarbon conversion is provided which is in the form of solid pieces containing at least one silica-containing material having a plate or sheet morphology and at least one separately prepared further material that is oxidic and has catalytic activity for hydrocarbon conversion.

Such silica-containing materials are preferably crystalline and include especially the lamellar zeolites classified by Breck (Zeolite Molecular Sieves, Wiley 1974, 128–132) as Group 7, for example heulandite and clinoptilolite. Preferably it includes or consists of FU-1, a silica-containing material made by hydrothermal reaction of a silica source and an alumina source in the presence of methylated quaternary ammonium compounds and having an X-ray diffraction pattern including the following characteristic lines:

TABLE 1

| d(A) | 100 I/Io | d(A) | 100 I/Io |
|------|----------|------|----------|
| 9.51 | 31 | 4.35 | 13 |
| 8.35 | 8 | 4.07 | 19 |
| 6.92 | 28 | 4.00 | 9.4 |
| 6.61 | 9 | 3.89 | 13 |
| 6.26 | 9 | 3.73 | 28 |
| 5.25 | 16 | 3.68 | 3 |
| 4.61 | 63 | 3.44 | 100 |
| 4.48 | 6 | | |

The morphology of FU-1, as shown by electron microscope examination, can be that of very thin sheets with considerable crumpling. Viewed at a magnification up to 500000 it is in very thin sheets of angularly interlocking platelets, typically 50 to 400 Å thick and agglomerated into packs of total thickness in the range 0.1 to 10 microns.

The chemical composition of FU-1 is as follows:

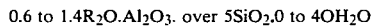

$0.6$ to $1.4 R_2O.Al_2O_3$. over $5SiO_2.0$ to $40H_2O$ where R is a monovalent cation or $1/n$ of a cation of valency n. The number of molecules of $SiO_2$ typically at least 10, for example 15 to 300 and especially 15 to 30 and up to 50. Freshly prepared FU-1 may contain also quaternary ("onium") compound, typically to the extent of 0.5 to 2.5 molecules, in excess of 1.4 molecules.

Further characterising features are reported in our co-pending application.

When the silica-containing plate or sheet material contains FU-1, it preferably contains at least 20% w/w especially at least 50% w/w thereof. The remainder of the plate or sheet material preferably includes zeolite nu-1, and this material is suitably the product of zeolite synthesis in conditions such that FU-1 and nu-1 are produced simultaneously.

The term "catalyst" includes the solid pieces at any stage after bringing their components together, for example (a) before or after ion-exchange, (b) before or after calcination or activation, (c) during use at full activity, (d) when partly or fully deactivated and (e) when partly or fully reactivated, and (f) after treatments such as by steam. Thus when the plate or sheet material is a zeolite of the onium type such as FU-1, it can contain all the onium compound present in it when freshly synthesised, or can contain a zero or smaller proportion of such compound or decomposition products of such a compound, either as a result of calcination before or after mixing with the active material or else as a result of calcination in the course of regeneration.

Either or both of plate or sheet material and the further material can be associated with a matrix material, which can be either inert or catalytically active. This may be present simply as a binding agent to hold the small zeolite particles (0.1 to 10 microns) together, or it may be added as a diluent to control the extent of conversion in a process in order, for example, to limit the rate of coke formation. The matrix can also strengthen the catalyst against the rigorous regeneration by oxidation of deposited coke. Typical inorganic matrix materials include catalyst support materials such as alumina, silica, zirconia and mixed or compound oxides such as clay minerals for example kaolin, bentonites, montmorillonites, sepiolite, attapulgite and Fuller's earth and synthetic compound silicates for example silica-alumina and silica-magnesia. In order to make effective use of the channels due to the plate or sheet material, the pieces preferably contain under 50% w/w of matrix material.

A further optional constituent of the catalyst is a material having catalytic activity for the oxidation of carbon or carbon monoxide, for example a transition metal (especially platinum or other platinum group metal at a concentration of 0.001 to 0.1%) or a transition metal oxide (especially an oxide of chromium, manganese, iron or cobalt) or an oxide of a rare-earth metal additional to any rare earth compounds introduced by ion-exchange into this or any component of the catalyst system.

Typically the size of the pieces is in the range 25 to 100 microns for a fluidised bed, under 2 mm for a liftable bed, or in the range 2–20 mm for a fixed bed.

The catalyst pieces can be made by simple mixing of their components. Any convenient order of mixing can be used, including methods that have been disclosed for making hydrocarbon cracking catalysts. They can be in any of the types of agglomerate in normal use, for example compressed pellets, extrusions, wet-granulated spheres, beads or spray-dried powder.

The relative proportions of plate or sheet material and the further material are chosen to suit the requirements of the conversion reaction. The possible range of choice is wide, for example in the range 2–98% of one and 98–2% of the other. These refer to active material, disregarding matrix material.

The further material is preferably at least one zeolite, and this is most useful in an acid form. Preferably at most 3%, especially less than 0.4%, of its lattice cation sites carry alkali metal ions. At least some of the remaining sites may carry either hydrogen ions (in the form in which these normally occur in zeolites) or hydrogen precursor ions (such as non-quaternary ammonium), since such precursor ions are readily decomposed to hydrogen ions on heating. Alternatively or additionally the remaining sites may carry ions of rare-earth metals, possibly mixed, as described below. Such hydrogen, hydrogen-precursor and rare-earth zeolites are of established value in catalysing transformations of certain hydrocarbons, but not primarily the heavy hydrocarbons to which the catalyst of the invention is especially applicable. Instead of or in addition to hydrogen and rare earth metal ions, the active zeolite may carry ions of one or more transition metals, particularly those from Periodic Groups IVA to VIII (including platinum group metals) and IB to VB, according to the Periodic Table published in "Abridgments of Specifications" by the UK Patent Office. Specific useful metal ions are those of zinc and manganese. Further, the active zeolite may carry ions of one or more of alkali earth metals and aluminium.

The silica-containing plate or sheet material may be ion-exchanged in the same manner as the active zeolite, but it is found that good results are obtained if it is mainly in the hydrogen form, with preferably at most 15% of its cation sites carrying alkali metal ions. The rare-earth and rare-earth/hydrogen forms are especially stable in repeated regeneration.

In another form of the invention the active zeolite contains cations chosen to modify its port size and thus its selective adsorptive properties.

It will be appreciated that the ion-exchange condition of the plates or sheet material and of any other materials present should be compatible with that of the active zeolite. In particular, if the active zeolite contains a low proportion of alkali metal ions, especially if it is in the hydrogen or hydrogen-precursor form, then the alkali metal ion content of the plate or sheet and other materials should also be preferably low, in order to prevent neutralisation of the acidity of the active zeolite.

It is within the invention to carry out ion exchange after the components of the catalyst system, including matrix materials if any, have been brought into the required intimate association. Consequently it is not necessary to take the preparation of a zeolite component of the composition beyond the stage at which it has crystallised, before mixing it with other materials to be present.

Any or all of the zeolite components can be treated, before or after mixing, in known steps, for example by steaming to adjust its activity, selectivity or thermal stability. Preferably an activation at 400°–500° C. for 1–24 hours is carried out before using the catalyst. The same conditions can be used, preferably in the presence of air, in order to reactivate the catalyst after use in a hydrocarbon conversion reaction. Some damage to the FU-1 structure may occur during such reactivation, but does not appear to decrease the value of the catalyst until it has become very severe.

Among the active zeolites that may be present are the following:

I. zeolites having ports of diameter in the range 6.5–15 Angstrom units, especially zeolites X, Y, L, offretite, mordenite and omega. Such zeolites are valuable as hydrocarbon cracking catalysts and a preferred active zeolite is rare-earth ion exchanged zeolite Y ("REY"), the rare earth being suitably a mixture of (by weight) cerium 45% as $CeO_2$, lanthanum 23% as $La_2O_3$, neodymium 16% as $Nd_2O_3$, praseodymium 10% as $Pr_2O_3$, samarium 4% as $Sm_2O_3$ and gadolinium 2.5% as $Gd_2O_3$;

II. zeolites having ports of diameter in the range 5.0–6.5 Angstrom units, especially zeolites of the ZSM-5 family (particularly ZSM 8, 11, 12 and 21, zeta-1 and zeta-3) and nu-1. These are valuable as catalysts for inter alia reactions involving single-ring aromatic hydrocarbons, for example alkylation and transalkylation of benzene and alkylbenzenes, especially the isomerisation of xylenes;

III. zeolites having ports smaller than 5.0 Angstrom units, especially zeolite A, chabazite and erionite. These are particularly valuable as adsorbents for small molecules such as water, $H_2S$, $NH_3$, $N_2$, $O_2$, $CO_2$, and are effective in separating or purifying fluids. Further, they can be used to catalyse reactions such as hydrogenation, isomerisation and oligomerisation of gaseous olefins.

Each of the above zeolites should, of course, be in the appropriate state of ion exchange.

As examples of hydrocarbon conversions that can be carried out using the catalyst there may be mentioned the following: catalytic cracking of hydrocarbons in a fixed, moving or fluidised bed at typically 400°–550° C.; the hydrocarbons to be used include especially middle distillate oils boiling in the range 200°–400° C. or part of that range, and heavy fractions including residua and crudes. Products in the naphtha range up to $C_{10}$ are formed in good yield;

catalytic reforming;

paraffin isomerisation;

isobutane alkylation;

alkylation of aromatic hydrocarbons, including the reaction of such hydrocarbons with olefins or alcohols, the isomerisation of xylenes and dimethylnaphthalenes and the disproportionation of toluene;

dealkylation of alkyl-substituted aromatic hydrocarbons.

When such reactions are carried out in the presence of hydrogen, for example as in hydrocracking or hydroisomerisation, the catalyst preferably contains one or more components providing a hydrogenation/dehydrogenation function, for example, one or more Group VIII metals, oxides or sulphides and, instead or in addition, one or more oxides or sulphides of metals of Group VIA or Group VIIA. Such components may be present in the plate or sheet material or the further component or both, may be in a state of ion-exchange or mere deposition or both.

In Examples 1 to 8 middle distillate oils are exemplified by hexadecane and decalin and crude and residual oils by tetralin and 1-methylnaphthalene.

Where percentages are specified these are by weight unless otherwise stated.

EXAMPLE 1

Preparation of H-FU-1/REY agglomerates (catalyst A)

The FU-1 was a sample of the product of Example 8 of our co-pending UK application cited above. As described therein, its composition was $$0.11Na_2O.1.07Q_2O.Al_2O_3.20SiO_2.3.7H_2O$$

(where Q is tetramethylammonium). Its X-ray diffraction pattern was as set out hereinabove and showed that it contained FU-1 without detectable impurity. A sample (5 g) of the zeolite was exchanged with 10 ml of 5% HCl for 5 hours at 90° C. It was then filtered, washed and dried at 90° C. In a second exchange it was treated with 60 ml 0.1 N HCl for 1 hour at 50° C., filtered, washed and dried at 90° C. It was then calcined in air at 450° C. Its composition % was:

| | |
|---|---|
| $SiO_2$ | 88.8 |
| $Al_2O_3$ | 6.4 |
| $Na_2O$ | 0.17 |
| N | 0.4 |
| C | 1.8 |
| loss, 1000° C. | 8.6 | indicating that about 1 in 25 of its cation sites were occupied by $Na^+$.

The REY was prepared by slurry-exchanging 40 g of sodium zeolite Y of composition $0.9Na_2O.Al_2O_3.5.2SiO_2.7H_2O$ (as dried at 100° C.) with 15 g of technical cerium chloride hexahydrate in 300 ml of water at 25° C. for 1 hour, then filtering and washing until no chloride could be detected in wash liquor, then drying for 3 hours at 250° C. The exchange procedure was repeated with fresh rare earth chloride. Finally the calcined material was slurry-exchanged with 300 ml of 5% ammonium sulphate for 1 hour at 90° C., filtered, washed with 600 ml of water and dried at 120° C. The dried product contained, on an anhydrous basis, 0.34% of $Na_2O$ and 17% of $RE_2O_3$, corresponding respectively to 2% and 80% of the cation sites.

(The technical cerium chloride was a mixture of rare earth chlorides having the composition, when expressed as oxides, stated hereinabove in the paragraph marked I).

To prepare the catalyst, 0.95 g of the exchanged calcined FU-1 (particle size 0.1 to 10 microns) was well mixed dry with 0.05 g of the REY and the mixture was pelleted dry into 3×3 mm cylinders by compression.

Preparation of comparison catalysts B, C, D

B: A commercial cracking catalyst (Houdry HZ-1) consisting of zeolite REY in a silica-alumina matrix was crushed and pelleted dry into 3×3 mm cylinders by compression.

C: Exchanged calcined FU-1 from A was pelleted dry without added material into 3×3 mm cylinders by compression.

D: A sample of the REY from A was well mixed dry with 19 times its weight of silica "KS300" as supplied by AKZO and pelleted dry into 3×3 mm cylinders by compression.

EXAMPLE 2

Paraffin cracking catalysed by catalysts A-D

Each catalyst (0.26 ml) was charged to a pulse microreactor and activated by heating at 450° C. for 1 hour in a current of air at 3 liters per hour, 2.7 atm. abs., pressure. Then the air was replaced by an equal nitrogen current and at 450° C. a 1-microliter sample of hexadecane was injected upstream of the catalyst. The gas leaving the catalyst was analysed by gas chromatography. The hydrocarbon product distribution, expressed as the percentage of the carbon atoms in each product class present as vapour in the catalyst effluent and also the percentage conversion and percentage yield are shown in Table 2. It is to be noted that as a consequence of the analytical technique used, the $C_8$-$C_{10}$ fraction includes some $C_7$ aromatics and the $C_{11}$-$C_{15}$ fraction includes some $C_{10}$ aromatics.

It is evident from Table 2 that the combination of FU-1 and REY (catalyst A) is more active than either of its constituent zeolites and more active than the commercial catalyst B. The low yield of fractions at and above $C_6$ using catalyst A indicates that it affords a high level of cracking severity.

TABLE 2

| Catalyst | A | B | C | D |
|---|---|---|---|---|
| Wt. (g) | 0.375 | 0.485 | 0.403 | 0.311 |
| Products % C atoms | | | | |
| <$C_6$ | 89.0 | 78.8 | 74.8 | 32.0 |
| $C_6 + C_7$ | 5.5 | 7.8 | 7.8 | 17.6 |
| $C_8 - C_{10}$ | 4.7 | 9.6 | 8.7 | 8.4 |
| $C_{11} - C_{15}$ | 0.5 | 3.0 | 1.3 | 4.53 |
| $C_{16}$ | 0.3 | 0.8 | 7.4 | 37.5 |
| Conversion (%) | 99.7 | 99.2 | 92.6 | 62.5 |
| Yields (%) | | | | |
| $C_6$ | 89 | 79 | 81 | 51 |
| $C_6 + C_7$ | 6 | 8 | 8 | 28 |
| $C_8 - C_{10}$ | 5 | 10 | 9 | 13 |
| $C_{11} - C_{15}$ | 0.5 | 3 | 1 | 7 |

EXAMPLE 3

Cycloparaffin cracking catalysed by catalysts A-D

Each catalyst was regenerated in the micro reactor by stopping the nitrogen current and passing a current of air at 3 liters per hour, 1 atm. abs. pressure, at 450° C. for 2 hours, by which time the catalyst was free of coke. Then the nitrogen current was restored and a 1 microliter sample of decalin (52% cis, 48% trans) was injected as in Example 2. The product distribution, percentage conversion and percentage yield are shown in Table 3.

It is evident that the zeolite mixture A according to the invention provides greater activity and catalytic severity than the comparison catalysts.

TABLE 3

| Catalyst | A | B | C | D |
|---|---|---|---|---|
| Wt (g) | 0.375 | 0.485 | 0.403 | 0.0311 |
| Products % C atoms | | | | |
| <$C_6$ | 53.9 | 51.2 | 38.1 | 8.3 |
| $C_6 + C_7$ | 12.4 | 12.6 | 14.9 | 10.0 |
| $C_8 - C_{10}$ | 32.2 | 34.4 | 26.2 | 23.4 |
| trans - decalin | 0.4 | 0.2 | 15.0 | 33.8 |
| cis - decalin | 1.1 | 1.6 | 5.8 | 24.6 |
| Conversion (%) | 98.5 | 98.2 | 79.2 | 41.7 |
| Yields (%) | | | | |
| <$C_6$ | 54.7 | 52.1 | 48.1 | 19.9 |
| $C_6 + C_7$ | 12.6 | 12.8 | 18.8 | 24.0 |
| $C_8 - C_{10}$ | 32.7 | 35.0 | 33.1 | 56.1 |

EXAMPLE 4

Aromatic hydrocarbon cracking over catalysts A–D

Example 3 was repeated except that the injected hydrocarbon was 1-methyl naphthalene. Table 4 shows the results: note that the $C_{11+}$ fraction reported does not include unconverted feed.

It is evident that catalyst A is the most active and has produced 70% more naphtha ($C_6$-$C_{10}$) than catalyst B despite its lower density. A weight of catalyst A equal to that of B would have produced 120% more naphtha.

TABLE 4

| Catalyst | A | B | C | D |
|---|---|---|---|---|
| Products % C atoms | | | | |
| $<C_6$ | 9.3 | 4.4 | 0.4 | 0.5 |
| $C_6 + C_7$ | 15.2 | 10.0 | 2.1 | 1.2 |
| $C_8 - C_{10}$ | 35.1 | 19.6 | 3.1 | 2.9 |
| $C_{11}+$ | 22.2 | 40.4 | 44.3 | 30.5 |
| 1-methylnaphthalene | 18.2 | 25.6 | 48.1 | 64.9 |
| Conversion (%) | 81.8 | 74.4 | 51.9 | 35.1 |
| Yields (%) | | | | |
| $<C_6$ | 11.4 | 5.9 | 0.8 | 1.4 |
| $C_6 + C_7$ | 18.6 | 13.4 | 4.0 | 3.4 |
| $C_8 - C_{10}$ | 42.9 | 26.3 | 6.0 | 8.3 |
| $C_{11}+$ | 27.1 | 54.3 | 85.3 | 86.9 |

EXAMPLE 5

Cycloalkane/aromatic hydrocarbon cracking over catalysts A–D

Example 3 was repeated except that the injected hydrocarbon was tetralin. Table 5 shows the results: note that the $C_{11+}$ fraction includes bicyclic compounds but not tetralin. Catalyst A is again the most active. It produces 26% more naphtha ($C_6$-$C_{10}$) than catalyst B, equivalent to 62% more if the weight of catalyst A were increased to equal that of B.

TABLE 5

| Catalyst | A | B | C | D |
|---|---|---|---|---|
| Products % carbon | | | | |
| $<C_6$ | 25.1 | 19.5 | 16.2 | 2.3 |
| $C_6 + C_7$ | 26.9 | 24.4 | 19.4 | 4.5 |
| $C_8 - C_{10}$ | 30.5 | 21.3 | 18.7 | 7.0 |
| $C_{11}$ | 8.0 | 10.9 | 22.6 | 24.2 |
| Tetralin | 9.5 | 23.9 | 23.1 | 62.0 |
| Conversion (%) | 90.5 | 76.1 | 76.9 | 38.0 |
| Yields (%) | | | | |
| $<C_6$ | 27.7 | 25.6 | 21.1 | 6.1 |
| $C_6 + C_7$ | 29.7 | 32.1 | 25.2 | 11.8 |
| $C_8 - C_{10}$ | 33.7 | 28.0 | 24.3 | 18.4 |
| $C_{11}+$ | 8.8 | 14.3 | 29.4 | 63.7 |

EXAMPLE 6

Gas oil cracking over catalysts A–D

Example 3 was repeated except that the injected hydrocarbon was an Ekofisk light gas oil (initial b.p. 205° C., final b.p. 390° C., mean average b.p. 300° C.). Table 6 shows the results. Catalyst A is the most active and has evidently provided a level of catalytic severity that is advantageous for making products under $C_6$ but is rather too high for making $C_6$-$C_{10}$ naphtha. This result is consistent with the paraffin cracking reported in Example 2. For naphtha production from this light gas oil a lower severity would be appropriate.

TABLE 6

| Catalyst | A | B | C | D |
|---|---|---|---|---|
| Products % C atoms | | | | |
| $<C_6$ | 59.6 | 55.9 | 43.3 | 12.1 |
| $C_6 + C_7$ | 10.3 | 10.9 | 12.9 | 13.9 |
| $C_8 - C_{10}$ | 20.8 | 21.7 | 18.5 | 16.4 |
| $C_{11}+^{9.3}$ | 11.5 | 25.3 | 57.7 | |
| Conversion (%) | 90.7 | 88.5 | 74.7 | 42.3 |
| Yields (%) | | | | |
| $<C_6$ | 65.7 | 63.2 | 58.0 | 28.6 |
| $C_6 + C_7$ | 11.4 | 12.3 | 17.3 | 32.9 |
| $C_8 - C_{10}$ | 22.9 | 24.5 | 24.8 | 38.8 |

EXAMPLE 7

Extent of deactivation during cracking of highly coking feedstock

Using the micro-reactor and conditions described in Example 3, catalysts A and B were compared in the following operating cycle:

1. 1 microliter of n-octane injected, products analysed;
2. 5 microliters of 1-methyl naphthalene injected (this feedstock has a low hydrogen to carbon ratio and is highly coking);
3. 30 minutes later, 1 microliter of n-octane injected, products analysed;
4. step 2 repeated;
5. step 3 repeated.

The percentage conversion was calculated from the analytical results and is set out in Table 7. It is evident that Catalyst A is initially more active than catalyst B and is less deactivated by the coking feedstock.

TABLE 7

| Catalyst | Percentage conversion | | |
| | Initial | step 3 | step 5 |
|---|---|---|---|
| A | 83.1 | 59.7 | 55.0 |
| B | 78.3 | 55.0 | 47.5 |

EXAMPLE 8

Catalyst E containing REY+RE-H-FU-1 and comparison catalysts

The FU-1 was a sample of the product of Example 24 of our co-pending U.S. application cited above. As described therein, its composition was:

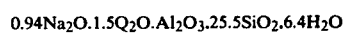
0.94Na$_2$O.1.5Q$_2$O.Al$_2$O$_3$.25.5SiO$_2$.6.4H$_2$O

Our co-pending application sets out its X-ray diffraction pattern. This sample was converted to the hydrogen form by the procedure described Example 1 but without calcination. The hydrogenation form, which still contained Q$_2$O, was slurried at 95° C. for 1 hour with a 10% solution of the technical cerium chloride used in Example 1 in the proportion of 25 g of the hexahydrate per 100 g of H-FU-1. The solid phase was collected on a filter, washed, dried at 100° C. for 17 hours and calcined at 450° C. in air for 48 hours. The product, now substantially free of Q$_2$O, was exchanged once more with the cerium chloride solution and calcined at 450° C. for 3 hours. Its composition was now

0.07Na$_2$O.0.18RE$_2$O$_3$.Al$_2$O$_3$.23SiO$_2$.9.8H$_2$O

To prepare the catalyst the RE-H-FU-1 and REY were mixed and pelleted as in Example 1. Comparison catalysts F–H F: as E but using the above H-FU-1 without the cerium chloride exchange;

G: (n5% of the REY, mixed and pelleted with 95% of amorphous silica-alumina cracking catalyst containing 12.5% $Al_2O_3$: this material was obtained commercially in bead form and crushed to pass a 72 BSS sieve (211 microns) before mixing with the REY;

H: 5% REY+47.5% of the above H-FU-1+47.5% of the above crushed silica-alumina.

EXAMPLE 9

Cracking over catalysts A and E–H

Using 4 different feedstocks in successive runs with intervening regeneration at 450° C. in air, Example 2 was repeated except that the inlet nitrogen pressure was 4.4 atm/abs.

(a) Hexadecane

The results are shown in Table 8. It is evident that catalysts A, E, F and H all gave higher yields of naphtha products than catalyst G containing the amorphous silica-alumina instead of FU-1. The REY/RE-H-FU-1 catalyst E gave least heavier hydrocarbon.

(b) Gas oil

Results using Ekofisk light gas oil (see Example 6) instead of hexadecane are shown in Table 9. All the catalysts containing FU-1 gave higher light naphtha ($C_6+C_7$) yields than catalyst G.

(c) Light cycle oil I

Results using a light cycle oil from a conventional catalytic cracking process (Phillips) are shown in Table 10. Catalyst E containing RE-H-FU-1 is considerably less active than catalyst G not containing FU-1, but catalysts A, F and H are not much less active. All the catalysts containing FU-1 give a better yield of hydrocarbons up to $C_7$ than does catalyst G.

(d) Light cycle oil II

Results using a Texaco light cycle oil are shown in Table 11. This oil is more difficult to crack than oil I, but the yield of light products is at least as high as when using catalyst G.

TABLE 8

| Feed | Hexadecane | | | | |
|---|---|---|---|---|---|
| Catalyst | A | E | F | G | H |
| Wt (g) | 0.444 | 0.465 | 0.441 | 0.396 | 0.417 |
| Products % C atoms | | | | | |
| $<C_6$ | 55.2 | 63.1 | 56.8 | 62.8 | 66.6 |
| $C_6 + C_7$ | 14.3 | 15.2 | 18.3 | 14.8 | 16.1 |
| $C_8 - C_{10}$ | 8.2 | 3.9 | 9.7 | 9.9 | 7.4 |
| $C_{11} - C_{15}$ | 10.2 | 1.5 | 8.0 | 11.3 | 1.4 |
| $C_{16}$ | 12.1 | 16.3 | 7.2 | 1.2 | 8.5 |
| Conversion (%) | 87.9 | 83.7 | 92.8 | 98.8 | 91.5 |
| Yields (%) | | | | | |
| $<C_6$ | 62.8 | 75.4 | 61.2 | 63.6 | 72.8 |
| $C_6 + C_7$ | 16.3 | 18.2 | 19.7 | 15.0 | 17.6 |
| $C_8 - C_{10}$ | 9.3 | 4.6 | 10.5 | 10.0 | 8.1 |
| $C_{11} - C_{15}$ | 11.6 | 1.8 | 8.6 | 11.4 | 1.5 |

TABLE 9

| Feed | Ekofisk light gas oil | | | | |
|---|---|---|---|---|---|
| Catalyst | A | E | F | G | H |
| Wt (g) | 0.444 | 0.465 | 0.441 | 0.396 | 0.417 |
| Products % C atoms | | | | | |
| $<C_6$ | 24.1 | 37.0 | 35.1 | 34.6 | 39.9 |
| $C_6 + C_7$ | 14.2 | 17.5 | 15.4 | 14.1 | 16.6 |
| $C_8 - C_{10}$ | 17.1 | 16.4 | 19.6 | 19.0 | 21.7 |
| $C_{11}^+$ | 44.6 | 29.1 | 29.9 | 32.3 | 21.8 |
| Conversion (%) | 55.4 | 70.9 | 70.1 | 67.7 | 78.2 |
| Yields (%) | | | | | |
| $<C_6$ | 43.5 | 52.2 | 50.1 | 51.1 | 51.0 |
| $C_6 + C_7$ | 25.6 | 24.7 | 22.0 | 20.8 | 21.2 |
| $C_8 - C_{10}$ | 30.9 | 23.1 | 27.9 | 28.1 | 27.8 |

TABLE 10

| Feed | light cycle oil I | | | | |
|---|---|---|---|---|---|
| Catalyst | A | E | F | G | H |
| Wt (g) | 0.44 | 0.465 | 0.441 | 0.396 | 0.417 |
| Products % C atoms | | | | | |
| $<C_6$ | 16.5 | 9.1 | 15.8 | 19.9 | 18.9 |
| $C_6 + C_7$ | 7.0 | 4.5 | 5.9 | 9.9 | 7.7 |
| $C_8 - C_{10}$ | 12.4 | 7.2 | 11.8 | 18.4 | 12.8 |
| $C_{11}^+$ | 64.1 | 79.2 | 66.5 | 51.8 | 60.6 |
| Conversion (%) | 35.9 | 20.8 | 33.5 | 48.2 | 39.4 |
| Yields (%) | | | | | |
| $<C_6$ | 46.0 | 43.8 | 47.2 | 41.3 | 48.0 |
| $C_6 + C_7$ | 19.5 | 21.6 | 17.6 | 20.5 | 19.5 |
| $C_8 - C_{10}$ | 34.5 | 34.6 | 35.2 | 38.2 | 32.5 |

TABLE 11

| Feed | light cycle oil II | | | |
|---|---|---|---|---|
| Catalyst | E | F | G | H |
| wt (g) | 0.465 | 0.441 | 0.396 | 0.417 |
| Products % C atoms | | | | |
| $<C_6$ | 18.9 | 13.9 | 18.9 | 18.7 |
| $C_6 + C_7$ | 5.3 | 5.4 | 8.0 | 6.4 |
| $C_8 - C_{10}$ | 13.5 | 15.9 | 22.7 | 18.6 |
| $C_{11}^+$ | 62.3 | 64.8 | 50.4 | 56.3 |
| Conversion (%) | 37.7 | 35.3 | 49.6 | 43.7 |
| Yields (%) | | | | |
| $<C_6$ | 50.1 | 39.5 | 38.1 | 42.8 |
| $C_6 + C_7$ | 14.1 | 15.3 | 16.1 | 14.6 |
| $C_8 - C_{10}$ | 35.8 | 45.2 | 45.8 | 42.6 |

EXAMPLE 10

Effect of Steam Treatment

The samples of catalyst E–H used in Example 9d, which had already been used in Examples 9a-c with intervening regeneration by heating at 450° C. for 2 hours, were calcined in steam at 1 atm abs pressure at 750° C. for 3 hours, to simulate deactivation in the regenerator of a fluid catalytic cracker. By X-ray diffusion it was shown that FU-1 was still present but had been partly converted to amorphous silica-alumina.

Successive runs using each of the 4 feedstocks were carried out over the steam-treated catalysts, with intervening regeneration as before. The results are shown in Tables 12–15 and the following deductions can be made:

Table 12: from hexadecane the ($C_6+C_7$) yield is higher using the catalysts containing FU-1;

Table 13: from the gas/oil the ($C_6+C_7$) yield and the $C_6$ to $C_{10}$ yield are both higher using the catalysts containing FU-1;

Table 14: from light cycle oil I the $C_6$ to $C_{10}$ yield is higher using the catalysts containing FU-1;

Table 15: from light cycle oil II the $C_6$ to $C_{10}$ yield using the catalysts containing FU-1 is at least as high as that obtained using the comparison catalyst G.

TABLE 12

| Feed | Hexadecane | | | |
|---|---|---|---|---|
| Catalyst | E | F | G | H |
| Wt (g) | 0.465 | 0.457 | 0.341 | 0.423 |
| Products % C atoms | | | | |
| <$C_6$ | 45.2 | 55.4 | 61.4 | 53.7 |
| $C_6 + C_7$ | 13.2 | 18.9 | 16.8 | 16.0 |
| $C_8 - C_{10}$ | 2.1 | 4.0 | 4.4 | 3.2 |
| $C_{11} - C_{15}$ | 0 | 0.2 | 0.2 | 0 |
| $C_{16}$ | 39.5 | 21.5 | 17.2 | 27.1 |
| Conversion (%) | 60.5 | 78.5 | 82.8 | 72.9 |
| Yields (%) | | | | |
| <$C_6$ | 74.7 | 70.6 | 74.1 | 73.7 |
| $C_6 + C_7$ | 21.8 | 24.1 | 20.3 | 21.9 |
| $C_8 - C_{10}$ | 3.5 | 5.1 | 5.3 | 4.4 |
| $C_{11} - C_{15}$ | 0 | 0.2 | 0.3 | 0 |

TABLE 13

| Feed | Ekofisk light gas oil | | | |
|---|---|---|---|---|
| Catalyst | E | F | G | H |
| Wt (g) | 0.465 | 0.457 | 0.341 | 0.423 |
| Products % C atoms | | | | |
| <$C_6$ | 19.9 | 21.0 | 20.5 | 23.5 |
| $C_6 + C_7$ | 11.7 | 14.5 | 18.0 | 14.2 |
| $C_8 - C_{10}$ | 16.2 | 14.1 | 19.8 | 17.2 |
| $C_{11}^+$ | 52.2 | 50.4 | 41.7 | 45.1 |
| Conversion (%) | 47.8 | 49.6 | 58.3 | 54.9 |
| Yields (%) | | | | |
| <$C_6$ | 41.6 | 42.4 | 44.7 | 42.8 |
| $C_6 + C_7$ | 24.5 | 29.2 | 26.3 | 25.9 |
| $C_8 - C_{10}$ | 33.9 | 28.4 | 29.0 | 31.3 |

TABLE 14

| Feed | Light cycle oil I | | | |
|---|---|---|---|---|
| Catalyst | E | F | G | H |
| Wt (g) | 0.465 | 0.457 | 0.341 | 0.423 |
| Products % C atoms | | | | |
| <$C_6$ | 9.1 | 10.3 | 16.9 | 12.6 |
| $C_6 + C_7$ | 4.5 | 4.3 | 6.9 | 5.3 |
| $C_8 - C_{10}$ | 7.2 | 6.9 | 10.7 | 8.9 |
| $C_{11}^+$ | 79.2 | 78.5 | 65.5 | 73.2 |
| Conversion (%) | 20.8 | 21.5 | 34.5 | 26.8 |
| Yields (%) | | | | |
| <$C_6$ | 43.8 | 47.9 | 49.0 | 47.0 |
| $C_6 + C_7$ | 21.6 | 20.0 | 20.0 | 19.8 |
| $C_8 - C_{10}$ | 34.6 | 32.1 | 31.0 | 33.2 |

TABLE 15

| Feed | light cycle oil II | | | |
|---|---|---|---|---|
| Catalyst | E | F | G | H |
| Wt (g) | 0.465 | 0.457 | 0.341 | 0.423 |
| Products % C atoms | | | | |
| <$C_6$ | 9.1 | 9.8 | 17.6 | 12.6 |
| $C_6 + C_7$ | 4.0 | 4.4 | 6.6 | 4.6 |
| $C_8 - C_{10}$ | 9.2 | 10.0 | 14.9 | 10.8 |
| $C_{11}^+$ | 77.7 | 75.8 | 60.9 | 72.0 |
| Conversion (%) | 22.3 | 24.2 | 39.1 | 28.0 |
| Yields (%) | | | | |
| <$C_6$ | 40.8 | 40.5 | 45.0 | 45.0 |
| $C_6 + C_7$ | 17.9 | 18.2 | 16.9 | 16.4 |
| $C_8 - C_{10}$ | 41.3 | 41.3 | 38.1 | 38.6 |

EXAMPLE 11

Catalysts I–M containing matrixed REY

The H-FU-1 and RE-H-FU-1 were further samples of the materials described in Example 8. The matrixed REY component was made by crushing to pass a 72 BSS sieve the bead-form commercial cracking catalyst "Houdry HFZ-20" which contains 25% of hydrogen zeolite Y. Each catalyst contained 20% of this REY component, along with the following other components:

I: 80% amorphous silica-alumina (comparison catalyst);
J: 80% H-FU-1;
K: 80% RE-H-FU-1;
L: 40% H-FU-1 and 40% amorphous silica-alumina;
M: 40% RE-H-FU-1 and 40% amorphous silica alumina.

Each was mixed and pelleted as described in Example 1.

EXAMPLE 12

Cracking over catalysts I—M

Example 9 was repeated using these catalysts.

(a) n-Hexadecane

From Table 16 is is evident that catalysts, J, K and M are more active than comparison catalyst I and that all the catalysts containing FU-1 gave higher yields of total naphtha ($C_6$-$C_{10}$) and lower yields of heavy products than catalyst I.

(b) Gas oil

From Table 17 is is evident that the catalysts containing FU-1 are more active than catalyst I and that they give a higher proportion of lighter products.

(c) Light cycle oil I

From Table 18 it is evident that catalysts J and K, in which the proportion of FU-1 is high, and L, in which the $^A$FU-1 content is lower but the hydrogen-form of it is present, are more active than catalyst I and give a higher proportion of lighter products.

(d) Light cycle oil II

From Table 19 it is evident that the catalysts containing FU-1 apart from L, are more active than comparison catalyst I, and that they all produce a higher proportion of lighter products.

Table 16

| Feed | Hexadecane | | | | |
|---|---|---|---|---|---|
| Catalyst | I | J | K | L | M |
| Wt (g) | 0.434 | 0.476 | 0.440 | 0.468 | 0.443 |
| Products % C atoms | | | | | |
| <$C_6$ | 67.8 | 72.1 | 75.3 | 58.8 | 69.8 |
| $C_6 + C_7$ | 9.7 | 16.1 | 14.5 | 13.2 | 14.8 |
| $C_8 - C_{10}$ | 8.1 | 7.9 | 8.4 | 7.6 | 8.8 |
| $C_{11} - C_{15}$ | 7.6 | 0.6 | 0.9 | 4.2 | 2.9 |
| $C_{16}$ | 6.8 | 3.3 | 0.9 | 16.2 | 3.7 |
| Conversion (%) | 93.2 | 96.7 | 99.1 | 83.8 | 96.3 |
| Yields (%) | | | | | |
| <$C_6$ | 72.7 | 74.5 | 76.0 | 70.2 | 72.5 |
| $C_6 + C_7$ | 10.4 | 16.6 | 14.6 | 15.7 | 15.4 |
| $C_8 - C_{10}$ | 8.7 | 8.2 | 9.1 | 9.1 | |
| $C_{11} - C_{15}$ | 8.2 | 0.6 | 0.9 | 5.0 | 3.0 |

TABLE 17

| Feed | Ekofisk light gas oil | | | | |
|---|---|---|---|---|---|
| Catalyst | I | J | K | L | M |
| Wt (g) | 0.434 | 0.476 | 0.440 | 0.468 | 0.443 |
| Products % C atoms | | | | | |
| <$C_6$ | 29.4 | 34.9 | 41.6 | 32.7 | 37.8 |
| $C_6 + C_7$ | 17.0 | 18.8 | 18.5 | 15.1 | 14.4 |
| $C_8 - C_{10}$ | 20.8 | 23.6 | 22.5 | 17.2 | 18.7 |
| $C_{11}^+$ | 32.8 | 22.7 | 17.4 | 35.0 | 29.1 |

TABLE 17-continued

| Feed | Ekofisk light gas oil | | | | |
|---|---|---|---|---|---|
| Catalyst | I | J | K | L | M |
| Conversion (%) | 67.2 | 77.3 | 82.5 | 65.0 | 70.9 |
| Yields (%) | | | | | |
| <C₆ | 43.8 | 45.2 | 50.4 | 50.3 | 53.3 |
| C₆ + C₇ | 25.3 | 24.3 | 22.4 | 23.3 | 20.3 |
| C₈ − C₁₀ | 30.9 | 30.5 | 27.2 | 26.5 | 26.4 |

TABLE 18

| Feed | light cycle oil I | | | | |
|---|---|---|---|---|---|
| Catalyst | I | J | K | L | M |
| Wt (g) | 0.434 | 0.476 | 0.440 | 0.468 | 0.443 |
| Products % C atoms | | | | | |
| <C₆ | 23.8 | 25.0 | 32.1 | 25.9 | 24.8 |
| C₆ + C₇ | 8.6 | 11.0 | 11.6 | 9.6 | 8.3 |
| C₈ − C₁₀ | 16.9 | 17.2 | 20.8 | 16.7 | 15.0 |
| C₁₁⁺ | 50.7 | 46.8 | 35.5 | 47.7 | 51.9 |
| Conversion (%) | 49.3 | 53.2 | 64.5 | 52.3 | 48.1 |
| Yields (%) | | | | | |
| <C₆ | 48.3 | 47.0 | 49.8 | 49.6 | 51.6 |
| C₆ + C₇ | 17.4 | 20.7 | 18.0 | 18.5 | 17.2 |
| C₈ − C₁₀ | 34.3 | 32.3 | 32.2 | 31.9 | 31.2 |

TABLE 19

| Feed | light cycle oil II | | | | |
|---|---|---|---|---|---|
| Catalyst | I | J | K | L | M |
| Wt (g) | 0.434 | 0.476 | 0.440 | 0.468 | 0.443 |
| Products % C atoms | | | | | |
| <C₆ | 18.9 | 22.9 | 27.2 | 19.7 | 24.8 |
| C₆ + C₇ | 8.0 | 7.0 | 9.7 | 6.2 | 7.5 |
| C₈ − C₁₀ | 22.7 | 23.6 | 23.3 | 16.3 | 19.9 |
| C₁₁⁺ | 50.4 | 46.5 | 39.8 | 57.8 | 47.8 |
| Conversion (%) | 49.6 | 53.5 | 60.2 | 42.2 | 52.2 |
| Yields (%) | | | | | |
| <C₆ | 38.1 | 42.8 | 45.2 | 46.7 | 47.5 |
| C₆ + C₇ | 16.1 | 13.1 | 16.1 | 14.7 | 14.4 |
| C₈ − C₁₀ | 45.8 | 44.1 | 38.7 | 38.6 | 38.1 |

We claim:

1. A catalyst for hydrocarbon conversion in the form of solid pieces containing at least one silica-containing material having a plate or sheet morphology which includes or consists of zeolite FU-1 having the chemical composition of $$\frac{0.6 \text{ to } 1.4 \text{ R}_2\text{O} \cdot \text{Al}_2\text{O}_3}{5 \text{ SiO}_2 \cdot 0 \text{ to } 40\text{H}_2\text{O}}$$

where R is a monovalent cation or 1/n of a cation of valency n and having an X-ray diffraction pattern substantially as set out in Table 1, and at least one separately prepared further material that is oxidic and has catalytic activity for hydrocarbon conversion.

2. A catalyst for hydrocarbon conversion in the form of solid pieces containing
A. At least one silica-containing material having a plate or sheet morphology which includes zeolite FU-1 having the chemical composition of:

$$\frac{0.6 \text{ to } 1.4 \text{ R}_2\text{O} \cdot \text{Al}_2\text{O}_3}{5\text{SiO}_2 \cdot 40 \text{ H}_2\text{O}}$$

Where R is a monovalent cation or 1/n of a cation of valency n, and having an X-ray diffraction pattern of the characteristic lines:

TABLE I

| d(A) | 100 I/Io | d(A) | 100 I/Io |
|---|---|---|---|
| 9.51 | 31 | 4.35 | 13 |
| 8.35 | 8 | 4.07 | 19 |
| 6.92 | 28 | 4.00 | 9.4 |
| 6.61 | 9 | 3.89 | 13 |
| 6.26 | 9 | 3.73 | 28 |
| 5.25 | 16 | 3.68 | 3 |
| 4.61 | 63 | 3.44 | 100 |
| 4.48 | 6 | | | and
B. At least one separately prepared further zeolite having ports of diameter in the range of 6.5 to 15 Angstrom units.

3. A catalyst according to claim 1 in which the silica-containing material contains at least 50% w/w of FU-1.

4. A catalyst according to claim 1 in which the further material is at least one zeolite in which at most 3% of its lattice cation sites carry alkali metal ions.

5. A catalyst according to claim 4 in which the zeolite carries ions of one or more of hydrogen, hydrogen precursor and rare earth metals.

6. A catalyst according to claim 4 in which the zeolite carriers ions of one or more transition metals.

7. A catalyst according to claim 1 in which the silica-containing material is in the hydrogen or hydrogen+-rare earth form with at most 15% of its cation sites carrying alkali metal ions.

8. A catalyst according to claim 1 in which the zeolite has ports of diameter in the range 6.5 to 15 Angstrom units.

9. A process of hydrocarbon conversion catalysed by a catalyst according to claim 1.

10. A process according to claim 9 which comprises catalytically cracking a hydrocarbon feedstock which contains a naphthalene derivative or is a middle distillate oil boiling in the range 200°–400° C.

* * * * *

UNITED STATES PATENT AND TRADEMARK OFFICE
CERTIFICATE OF CORRECTION

PATENT NO. : 4,197,186
DATED : April 8, 1980
INVENTOR(S) : Glyn D. SHORT; Michael S. SPENCER; Thomas V. WHITTAM It is certified that error appears in the above-identified patent and that said Letters Patent are hereby corrected as shown below:

Column 13, line 47 (Claim 1) and column 14, line 10 (Claim 2) the formula should read as follows:

$$0.6 \text{ to } 1.4 \ R_2O \cdot Al_2O_3 \cdot \text{over } 5 \ SiO_2 \cdot 0 \text{ to } 40 \ H_2O$$

Signed and Sealed this

Twenty-sixth Day of August 1980

[SEAL]

Attest:

SIDNEY A. DIAMOND

Attesting Officer

Commissioner of Patents and Trademarks